United States Patent
Peled et al.

(10) Patent No.: US 7,113,566 B1
(45) Date of Patent: Sep. 26, 2006

(54) ENHANCING RESOLUTION OF X-RAY MEASUREMENTS BY SAMPLE MOTION

(75) Inventors: Asher Peled, Kfar Vradim (IL); Isaac Mazor, Haifa (IL); Boris Yokhin, Nazareth Illit (IL)

(73) Assignee: Jordan Valley Applied Radiation Ltd., Midal Ha 'Emek (IL)

( * ) Notice: Subject to any disclaimer, the term of this patent is extended or adjusted under 35 U.S.C. 154(b) by 0 days.

(21) Appl. No.: 11/181,746

(22) Filed: Jul. 15, 2005

(51) Int. Cl.
*G01N 23/20* (2006.01)
*G21K 1/04* (2006.01)
*H05G 1/00* (2006.01)

(52) U.S. Cl. .................. 378/70; 378/160; 378/208
(58) Field of Classification Search .................. 378/6, 378/7, 70, 79, 86–90, 160, 208
See application file for complete search history.

(56) References Cited

U.S. PATENT DOCUMENTS

| | | |
|---|---|---|
| 5,619,548 A | 4/1997 | Koppel |
| 5,740,226 A | 4/1998 | Komiya et al. |
| 6,381,303 B1 | 4/2002 | Vu et al. |
| 6,453,006 B1 * | 9/2002 | Koppel et al. ............... 378/86 |
| 6,512,814 B1 | 1/2003 | Yokhin et al. |
| 6,639,968 B1 | 10/2003 | Yokhin et al. |
| 6,754,305 B1 | 6/2004 | Rosencwaig et al. ......... 378/89 |
| 6,771,735 B1 * | 8/2004 | Janik et al. .................... 378/70 |
| 6,813,338 B1 | 11/2004 | Takata et al. |
| 6,823,043 B1 * | 11/2004 | Fewster et al. ............... 378/86 |
| 2001/0043668 A1 | 11/2001 | Hayashi et al. |
| 2002/0097837 A1 * | 7/2002 | Fanton et al. ................ 378/82 |
| 2003/0157559 A1 * | 8/2003 | Omote et al. ................ 435/7.1 |
| 2004/0109531 A1 * | 6/2004 | Yokhin et al. ................ 378/54 |
| 2004/0131151 A1 | 7/2004 | Berman et al. |

* cited by examiner

*Primary Examiner*—Edward J. Glick
*Assistant Examiner*—Irakli Kiknadze
(74) *Attorney, Agent, or Firm*—Smith, Gambrell & Russell, LLP

(57) ABSTRACT

A method for inspection of a sample includes directing a beam of X-rays toward a sample and configuring an array of detector elements to capture the X-rays scattered from the sample. The sample is shifted in a direction parallel to the axis of the array between at least first and second positions, which positions are separated one from another by an increment that is not an integer multiple of the pitch of the array. At least first and second signals are generated by the detector elements responsively to the X-rays captured thereby while the sample is in at least the first and second positions, respectively. The first and second signals are combined so as to determine an X-ray scattering profile of the sample as a function of position along the axis.

14 Claims, 2 Drawing Sheets

ENHANCING RESOLUTION OF X-RAY MEASUREMENTS BY SAMPLE MOTION

CROSS-REFERENCE TO RELATED APPLICATION

This application is related to U.S. patent application Ser. No. 10/689,314, filed Oct. 20, 2003, and published Jul. 8, 2004, as US 2004/0131151 A1. This related application is assigned to the assignee of the present patent application, and its disclosure is incorporated herein by reference.

FIELD OF THE INVENTION

The present invention relates generally to analytical instruments, and specifically to instruments and methods for analysis of material properties using X-rays.

BACKGROUND OF THE INVENTION

X-ray reflectometry (XRR) is a well-known technique for measuring the thickness, density and surface quality of thin film layers deposited on a substrate. Measurement of X-ray intensity reflected from the sample as a function of angle gives a pattern of interference fringes, which is analyzed to determine the properties of the film layers responsible for creating the fringe pattern. The X-ray intensity measurements are commonly made using a position-sensitive detector, such as a proportional counter or an array detector, typically a photodiode array or charge-coupled device (CCD).

A method for analyzing X-ray reflectance data to determine film thickness is described, for example, in U.S. Pat. No. 5,740,226, to Komiya et al., whose disclosure is incorporated herein by reference. After measuring X-ray reflectance as a function of angle, an average reflectance curve is fitted to the fringe spectrum. The average curve is based on a formula that expresses attenuation, background and surface roughness of the film. The fitted average reflectance curve is then used in extracting the oscillatory component of the fringe spectrum. This component is Fourier transformed to find the film thickness.

U.S. Pat. No. 5,619,548, to Koppel, whose disclosure is incorporated herein by reference, describes an X-ray thickness gauge based on reflectometric measurement. A curved, reflective X-ray monochromator is used to focus X-rays onto the surface of a sample. A position-sensitive detector, such as a photodiode detector array, senses the X-rays reflected from the surface and produces an intensity signal as a function of reflection angle. The angle-dependent signal is analyzed to determine properties of the structure of a thin film layer on the sample, including thickness, density and surface roughness.

U.S. Pat. Nos. 6,512,814 and 6,639,968, to Yokhin et al., whose disclosures are incorporated herein by reference, describe reflectometry apparatus that includes a radiation source, adapted to irradiate a sample with radiation over a range of angles relative to a surface of the sample, and a detector assembly, positioned to receive the radiation reflected from the sample over the range of angles and to generate a signal responsive thereto. A shutter is adjustably positionable to intercept the radiation. The shutter has a blocking position, in which it blocks the radiation in a lower portion of the range of angles, thereby allowing the reflected radiation to reach the array substantially only in a higher portion of the range, and a clear position, in which the radiation in the lower portion of the range reaches the array substantially without blockage.

Another common method of X-ray reflectometric measurement is described, for example, in an article by Naudon et al., entitled "New Apparatus for Grazing X-ray Reflectometry in the Angle-Resolved Dispersive Mode," in *Journal of Applied Crystallography* 22 (1989), p. 460, which is incorporated herein by reference. A divergent beam of X-rays is directed toward the surface of a sample at grazing incidence, and a detector opposite the X-ray beam source collects reflected X-rays. A knife edge is placed close to the sample surface immediately above a measurement location in order to cut off the primary X-ray beam. A monochromator between the sample and the detector (rather than between the source and sample, as in U.S. Pat. No. 5,619,548) selects the wavelength of the reflected X-ray beam that is to reach the detector.

XRR may also be used in situ, within a deposition furnace, to inspect thin film layers in production on a semiconductor wafer, as described, for example, by Hayashi et al., in U.S. Patent Application Publication US 2001/0043668 A1, whose disclosure is incorporated herein by reference. The furnace is provided with X-ray incidence and extraction windows in its side walls. The substrate upon which the thin film has been deposited is irradiated through the incidence window, and the X-rays reflected from the substrate are sensed through the X-ray extraction window.

U.S. Pat. No. 6,813,338, to Takata et al., describes a method for high-resolution powder diffraction using high-energy synchrotron radiation as an X-ray source. A detector mounted on a measuring instrument, such as a diffractometer, is moved by smaller distances than the distance between adjacent X-ray detection units (pixels). The measured data are interpolated to improve the spatial resolution of the measurement.

SUMMARY OF THE INVENTION

Embodiments of the present invention provide methods and systems for performing X-ray scattering measurements with enhanced resolution. These methods and systems are particularly advantageous in XRR-based analysis of thin film layers, and are also useful in other areas of angle-resolved X-ray scattering analysis. In the context of the present patent application and in the claims, the term "scattering" includes any and all types of X-ray emission from a sample induced by an incident X-ray beam, including XRR, X-ray diffraction (XRD) and X-ray fluorescence (XRF), as well as various types of diffuse X-ray scattering.

In embodiments of the present invention, an array of X-ray detector elements is used to measure angle-resolved X-ray scattering patterns with sub-pixel resolution. For this purpose, the sample is irradiated by an X-ray beam. The array is positioned and oriented so that the elements of the array receiving and resolve the radiation scattered from the sample as a function of position along an axis of the array. The sample is then translated in a direction parallel to the axis by an increment that is a non-integer multiple of the pitch of the array, and the measurement is repeated. Typically, the increment is equal to an integer fraction of the pitch of the array (pitch/n, wherein n is an integer), and the measurement is repeated at n different positions of the array along the axis. The scattering measurements made at the different positions are combined, typically by interleaving the measurements taken at the different increments, in order to obtain a scattering spectrum with enhanced resolution.

There is therefore provided, in accordance with an embodiment of the present invention, a method for inspection of a sample, including:

directing a beam of X-rays toward a sample;

configuring an array of detector elements, which are arranged along an array axis and mutually separated by a predetermined pitch, to capture the X-rays scattered from the sample;

shifting the sample in a direction parallel to the array axis between at least first and second positions, which positions are separated one from another by an increment that is not an integer multiple of the pitch;

receiving at least first and second signals generated by the detector elements responsively to the X-rays captured thereby while the sample is in at least the first and second positions, respectively; and combining at least the first and second signals so as to determine an X-ray scattering profile of the sample as a function of position along the axis.

In a disclosed embodiment, combining at least the first and second signals includes interleaving the signals.

Typically, the increment is less than or equal to one half of the pitch.

In some embodiments, directing the beam includes focusing the X-rays over a range of angles onto the sample, and configuring the array includes capturing the X-rays reflected from the sample, and combining at least the first and second signals includes determining an angular spectrum of X-ray reflectance.

In a disclosed embodiment, directing the beam includes configuring a shutter assembly to reduce a transverse dimension of the beam, and shifting the shutter assembly in conjunction with shifting the sample. Typically, configuring the shutter assembly includes positioning a knife edge at a selected distance from a surface of the sample, and shifting the shutter assembly includes moving the knife edge in conjunction with shifting the sample so as to maintain the selected distance between the knife edge and the surface.

Additionally or alternatively, combining at least the first and second signals includes assessing a non-uniformity of the beam of X-rays, and correcting the scattering profile to account for the non-uniformity.

There is also provided, in accordance with an embodiment of the present invention, apparatus for inspection of a sample, including:

an X-ray source, which is arranged to direct a beam of X-rays toward a sample;

an array of detector elements, which are arranged along an array axis and mutually separated by a predetermined pitch, and which are arranged to capture the X-rays scattered from the sample;

a motion stage, which is adapted to move the sample in a direction parallel to the array axis between at least first and second positions, which positions are separated one from another by an increment that is not an integer multiple of the pitch; and a processor, which is coupled to receive at least first and second signals generated by the detector elements responsively to the X-rays captured thereby while the sample is in at least the first and second positions, respectively, and which is operative to combine at least the first and second signals so as to determine an X-ray scattering profile of the sample as a function of position along the axis.

The present invention will be more fully understood from the following detailed description of the embodiments thereof, taken together with the drawings in which:

DETAILED DESCRIPTION OF EMBODIMENTS

Figure 1:
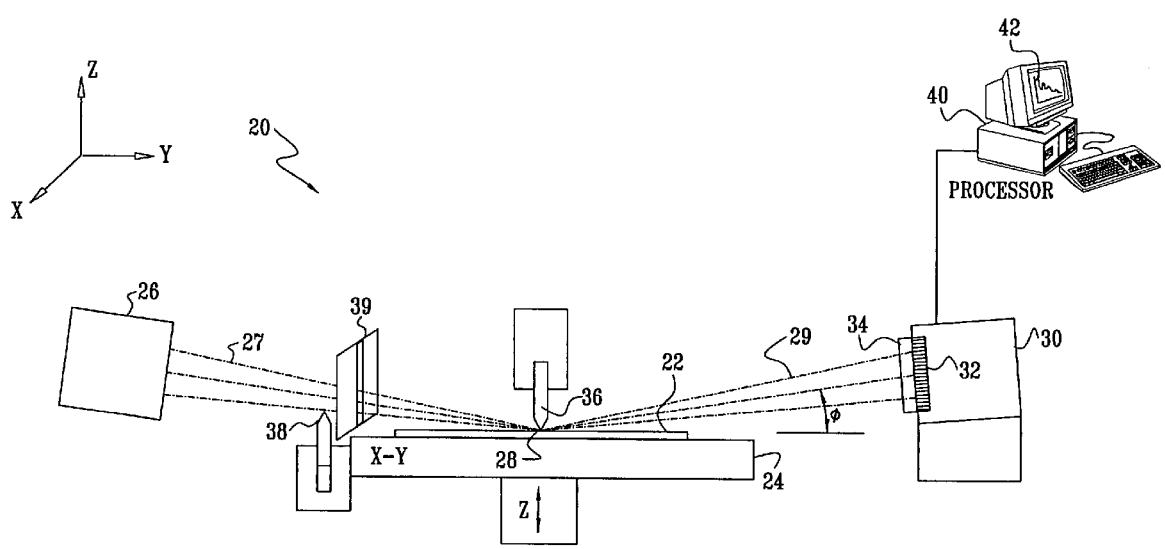
FIG. 1 is a schematic side view of a system for performing X-ray reflectometry (XRR) measurements on a sample, in accordance with an embodiment of the present invention.

Reference is now made to FIG. 1, which is a schematic side view of a system 20 for X-ray reflectometry (XRR), in accordance with an embodiment of the present invention. System 20 is similar to the XRR system described in the above-mentioned U.S. Pat. No. 6,512,814 and Patent Application Publication US 2004/0131151 A1, with the addition of features and capabilities described herein.

A sample 22, such as a semiconductor wafer, to be evaluated by system 20 is mounted on a motion stage 24, allowing accurate adjustment of its position and orientation. The position adjustment of stage 24 typically includes both horizontal (X-Y) and vertical (Z) motion, wherein the horizontal plane is defined as the plane of the sample surface. An X-ray source 26, typically an X-ray tube with suitable monochromatizing optics (not shown), irradiates a small area 28 on sample 22. The optics focus the radiation from the X-ray tube onto area 28 in a converging beam 27. A number of different optical configurations that may be used in source 26 are described in U.S. Pat. No. 6,381,303, whose disclosure is incorporated herein by reference. For example, the optics may comprise a curved crystal monochromator, such as the Doubly-Bent Focusing Crystal Optic, produced by XOS Inc., of Albany, N.Y. Other suitable optics are described in the above-mentioned U.S. Pat. Nos. 5,619,548 and 5,923,720. Further possible optical configurations will be apparent to those skilled in the art. A typical X-ray energy for reflectometric and scattering measurements in system 20 is about 8.05 keV (CuKal). Alternatively, other energies may be used, such as 5.4 keV (CrKal).

A dynamic knife edge 36 and shutter 38 are used to limit the extent of incident beam 27 of the X-rays in the vertical direction, while a slit 39 may be used to limit the beam horizontally. The knife edge, shutter and slit (or a subset of these elements, if not all are used in the system) together serve as a shutter assembly, for adjusting the transverse dimensions of beam 27. The use of knife edge 36 and shutter 38 in XRR measurements is described in detail in the above-mentioned U.S. Pat. No. 6,512,814. The configuration of the shutter assembly in FIG. 1 is shown by way of example, and alternative arrangements of X-ray optics for controlling the transverse dimensions of beam 27 in the manner described hereinbelow will be apparent to those skilled in the art and are considered to be within the scope of the present invention.

A reflected beam 29 of X-rays from sample 22 is collected by a detector assembly 30. Typically, for XRR, assembly 30 collects reflected X-rays over a range of reflection angles in the vertical (elevation—$\phi$) direction between about 0° and 3°, both below and above the critical angle of the sample for total external reflection. (For clarity of illustration, the angles shown in the figures are exaggerated, as is the elevation of source 26 and detector assembly 30 above the plane of sample 22 in FIG. 1.)

Assembly 30 comprises a detector array 32, such as a CCD array, as described hereinbelow. Although for simplicity of illustration, only a single row of detectors elements is shown in the figures, with a relatively small number of detector elements, array 32 generally includes a greater number of elements, arranged as either a linear array or a matrix (two-dimensional) array. Assembly 30 typically comprises a window 34 made of a suitable X-ray transparent material, such as beryllium, spaced in front of the detector array, between the array and the sample. Further details of the structure and operation of array 32 are described below with reference to FIG. 2.

A signal processor 40 analyzes the output of assembly 30, so as to determine a distribution 42 of the flux of X-ray photons reflected from sample 22 as a function of angle at a given energy or over a range of energies. Typically, sample 22 has one or more thin surface layers, such as thin films, at area 28, so that distribution 42 as a function of elevation angle exhibits an oscillatory structure due to interference effects among reflected X-ray waves from the interfaces between the layers. Processor 40 analyzes characteristics of the angular distribution in order to determine characteristics of one or more of the surface layers of the sample, such as the thickness, density and surface quality of the layer, using methods of analysis described hereinbelow.

Figure 2A:
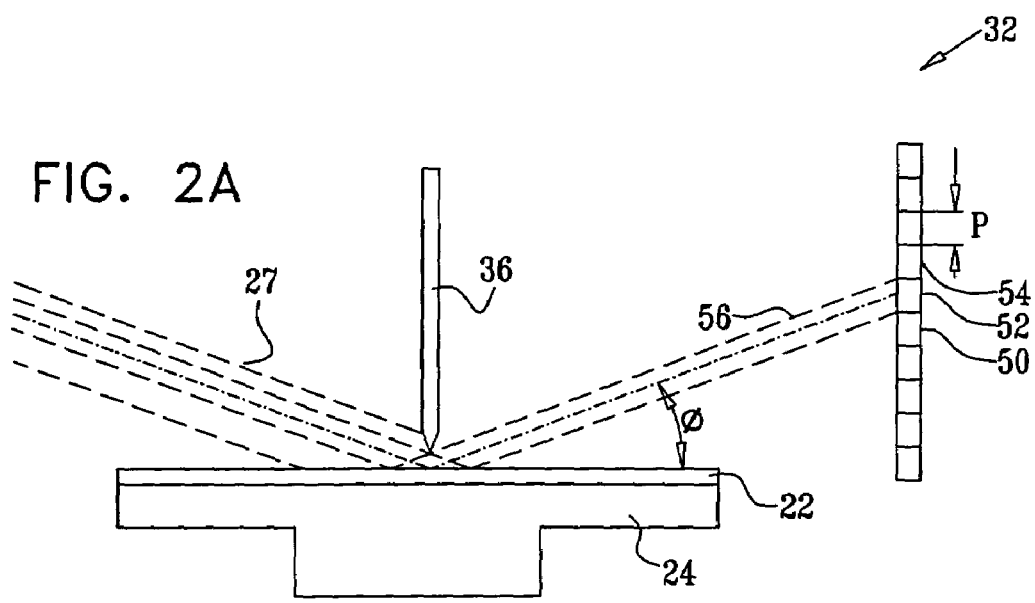
FIGS. 2A and 2B are schematic side views showing details of the system of FIG. 1 in two different positions of the sample, in accordance with an embodiment of the invention.

FIG. 2A is a schematic side view showing details of system 20, in accordance with an embodiment of the invention. Array 32 is seen to comprise detector elements 50, 52, 54, . . . , arranged along a vertical array axis. The detector elements are separated by a certain pitch, P, defined as the center-to-center distance between the elements. Typically, P is on the order of 24 µm. The elevation angle $\phi$ of an X-ray beam 56 reflected from the surface of sample 22 and received by a given detector element translates into the Z-coordinate of the detector element along the array axis according to the relation $\phi=\tan^{-1}Z/d \cong Z/d$, wherein d is the horizontal distance from the reflection point of the X-rays to array 32. For simplicity and clarity of illustration, incident beam 27 is shown in FIG. 2A as a parallel beam, with only a single angular component of the reflected beam. Embodiments of the present invention may indeed be applied in systems using collimated X-ray irradiation, such as systems for measurement of diffuse scattering characteristics. In system 20, however, as shown in FIG. 1, beam 27 typically converges onto sample 22, and thus gives rise to a reflected beam that diverges over a range of elevation angles. Beam 56 thus represents a single angular component of this diverging beam.

The angular resolution of array 32 is determined by the pitch P. In other words, in the absence of the resolution-enhancement techniques described hereinbelow, the angular resolution of array 32 is approximately P/d. Typically, given the limitations of available X-ray focusing optics, the focal diameter of beam 27 is greater than P. In order to improve the focal quality of the beam, knife edge 36 is brought into close proximity with the surface of sample 22 so as to cut off a portion of incident beam 27. Based on simple geometrical considerations, as shown in FIG. 2A, if the knife edge is held at a distance h above the surface of the sample, the angular resolution of reflected beam 56 will be approximately 2h/D. In other words, the closer the knife edge is held to the surface, the finer will be the resolution of the reflected beam, although this enhanced resolution comes at the expense of reduction in reflected beam intensity. Typically, the knife edge is set at approximately h=P/2, so that the resolution of the reflected beam is roughly equal to the resolution of array 32. Alternatively, h may be set to a different value, such as a value less than P/2 for finer resolution.

Figure 2B:
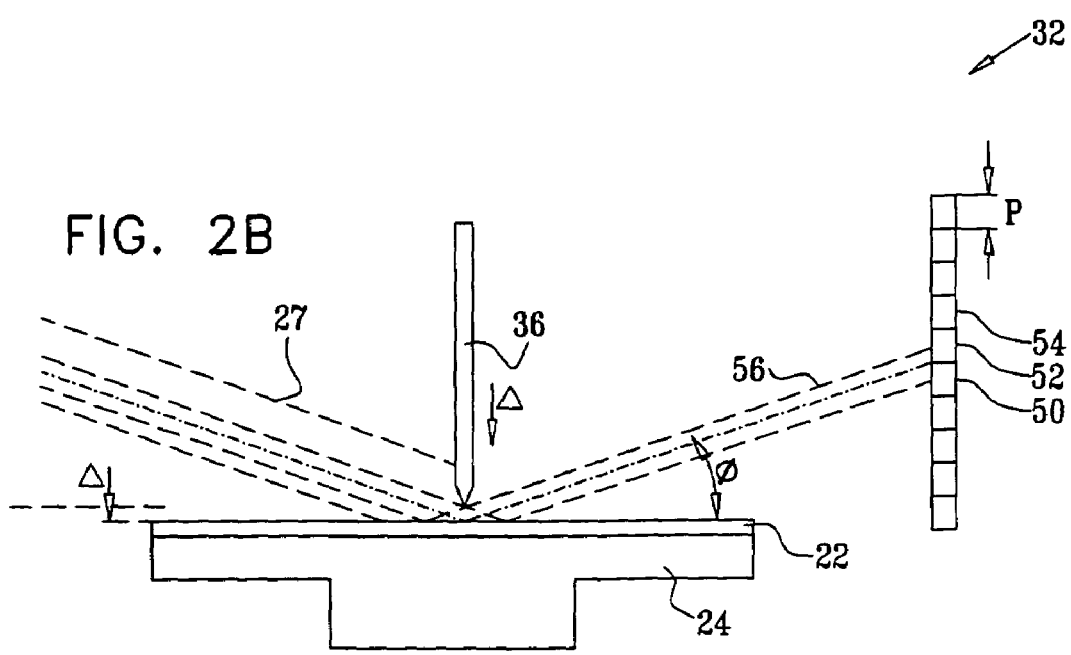

FIG. 2B is a schematic side view showing the effect of a downward (−Z) shift of sample 22 by a distance Δ, in accordance with an embodiment of the invention. The sample is shifted using the Z-direction adjustment of stage 24, without changing the X or Y position. In this example, Δ=P/2, but smaller or larger shifts, both downward and upward, may be made in like manner. In order to maintain the desired angular resolution of reflected beam 56, knife edge 36 is shifted downward by the same distance Δ as the sample. As a result, the angular scale of reflected beam 56 relative to the elements of array 32 is similarly shifted downward by half a pixel, i.e., by P/2. This shift is equivalent to shifting array 32 upward by half a pixel, as described in the above-mentioned US 2004/0131151 A1. In system 20, however, this shift is achieved without the need for precise motion control of detector assembly 30, but rather by taking advantage of the motion capabilities of stage 24. A stage of this sort is required for accurate alignment of the sample in most precision X-ray measurement systems in any case.

With sample 22 held in each of the positions shown in FIGS. 2A and 2B, source 26 is actuated, and assembly 30 captures the X-rays reflected from sample 22 as a function of the elevation angle. Assembly 30 may be operated in this manner to capture X-rays at more than two different vertical positions of the sample, typically with a smaller Z-direction increment between the positions. For example, three different positions separated by P/3 the array pitch may be used.

The signals generated by assembly 30 in each different vertical position are input to processor 40, which combines the readings made at the different positions into a single spectrum. In a sense, the processor creates a "virtual array," with finer resolution than the actual, physical array 32. The signals in the virtual array can be derived, for example, simply by interleaving the readings made in the different array positions. Thus, for each "virtual pixel" in the virtual array, processor 40 selects the measurement value of a real pixel at the corresponding position relative to the sample in one of the actual measurements, alternating from one virtual pixel to the next among the readings made in the different measurement positions.

In other words, assume the following pixel readings were made in three successive positions of sample 22:

Position 1: R11, R21, R31, R41, . . .
Position 2: R12, R22, R32, R42, . . .
Position 3: R13, R23, R33, R43, . . .

The resultant virtual array will then contain the following values, at virtual pixels separated by ⅓ the actual array pitch:

R11, R12, R13, R21, R22, R23, R31, R32, R33, R41, . . .

Alternatively, other methods, such as signal differentiation or summing of the readings in the different array positions, may be used to extract XRR information from the individual, actual measurements before combining them, or to select the actual measurement result to be used in each pixel of the virtual array. Processor 40 may then analyze the enhanced-resolution XRR spectrum to determine properties of the sample, such as the thickness, density and surface roughness of thin film layers on the sample.

Typically, stage 24 shifts sample 22 between the different vertical positions while X-ray source 26 remains stationary. Consequently, as illustrated in FIGS. 2A and 2B, a different portion of incident beam 27 is reflected into reflected beam 56 in each position. The remainder of beam 27 is blocked in each case by knife edge 36. Because of limitations of the X-ray tube and focusing optics in source 26, the intensity of beam 27 is typically not uniform over the entire beam profile. This non-uniformity may cause spurious variations in the measured intensity of the reflected beam between the different sample positions. (For example, R11, R21, . . . , may be consistently greater than R12, R22, . . . .)

To overcome this problem, the intensity profile of beam 27 may be measured and used to calculate correction factors to be applied to the signals measured in each different vertical position of the sample. As one example, a smooth test sample could be mounted on stage 24, and the intensity of reflected X-rays measured at array 32 as a function of angle in all vertical positions of interest. Variations in the intensity between the vertical positions can thus determined as a function of the angle and calibrated out of the actual sample measurements. Other methods for measurement and calibration of X-ray beam non-uniformities that may be used for this purpose, *mutatis mutandis*, are described, for instance, in U.S. patent application Ser. No. 11/000,044, filed Dec. 1, 2004, which is assigned to the assignee of the present patent application and whose disclosure is incorporated herein by reference.

The resolution-enhancement techniques described hereinabove are useful particularly when the XRR spectrum has a fine structure with high spatial frequency, so that the fringe separation is comparable to or smaller than the array pitch. Alternatively, the principles of the present invention can similarly be used in other types of angle-resolved X-ray scattering measurement, such as XRD, XRF and diffuse X-ray scattering, as well as in other types of radiation-based analysis. Moreover, elements of the apparatus in system 20 and the methods described hereinabove may be integrated into a fabrication chamber or cluster tool for purposes of in situ X-ray measurement, in the manner described in the above-mentioned US 2001/0043668 A1 or US 2004/0131151 A1.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for inspection of a sample, comprising:
   directing a beam of X-rays toward a sample;
   configuring an array of detector elements, which are arranged along an array axis and mutually separated by a predetermined pitch, to capture the X-rays scattered from the sample with an array resolution defined by the pitch;
   shifting the sample in a direction parallel to the array axis between at least first and second positions, which positions are separated one from another by an increment that is not an integer multiple of the pitch;
   receiving at least first and second signals generated by the detector elements responsively to the X-rays captured thereby while the sample is in at least the first and second positions, respectively; and
   combining at least the first and second signals so as to determine an X-ray scattering profile of the sample as a function of position along the axis with a profile resolution finer than the array resolution.

2. The method according to claim 1, wherein combining at least the first and second signals comprises interleaving the signals.

3. The method according to claim 1, wherein the increment is less than or equal to one half of the pitch.

4. The method according to claim 1, wherein directing the beam comprises focusing the X-rays over a range of angles onto the sample, and wherein configuring the array comprises capturing the X-rays reflected from the sample, and wherein combining at least the first and second signals comprises determining an angular spectrum of X-ray reflectance.

5. The method according to claim 1, wherein combining at least the first and second signals comprises assessing a non-uniformity of the beam of X-rays, and correcting the scattering profile to account for the non-uniformity.

6. A method for inspection of a sample, comprising:
   directing a beam of X-rays toward a sample;
   configuring an array of detector elements, which are arranged along an array axis and mutually separated by a predetermined pitch, to capture the X-rays scattered from the sample;
   shifting the sample in a direction parallel to the array axis between at least first and second positions, which positions are separated one from another by an increment that is not an integer multiple of the pitch;
   receiving at least first and second signals generated by the detector elements responsively to the X-rays captured thereby while the sample is in at least the first and second positions, respectively; and
   combining at least the first and second signals so as to determine an X-ray scattering profile of the sample as a function of position along the axis,
   wherein directing the beam comprises configuring a shutter assembly to reduce a transverse dimension of the beam, and shifting the shutter assembly in conjunction with shifting the sample.

7. The method according to claim 6, wherein configuring the shutter assembly comprises positioning a knife edge at a selected distance from a surface of the sample, and wherein shifting the shutter assembly comprises moving the knife edge in conjunction with shifting the sample so as to maintain the selected distance between the knife edge and the surface.

8. Apparatus for inspection of a sample, comprising:
   an X-ray source, which is arranged to direct a beam of X-rays toward a sample;
   an array of detector elements, which are arranged along an array axis and mutually separated by a predetermined pitch, and which are arranged to capture the X-rays scattered from the sample with an array resolution defined by the pitch;
   a motion stage, which is adapted to move the sample in a direction parallel to the array axis between at least first and second positions, which positions are separated one from another by an increment that is not an integer multiple of the pitch; and
   a processor, which is coupled to receive at least first and second signals generated by the detector elements responsively to the X-rays captured thereby while the sample is in at least the first and second positions, respectively, and which is operative to combine at least the first and second signals so as to determine an X-ray scattering profile of the sample as a function of position along the axis with a profile resolution finer than the array resolution.

9. The apparatus according to claim 8, wherein the processor is adapted to combine at least the first and second signals by interleaving the signals.

10. The apparatus according to claim 8, wherein the increment is less than or equal to one half of the pitch.

11. The apparatus according to claim 8, wherein the X-ray source is adapted to focus the X-rays over a range of angles onto the sample, and wherein the array is arranged to capture the X-rays reflected from the sample, so that the processor determines an angular spectrum of X-ray reflectance.

12. The apparatus according to claim 8, wherein the processor is adapted to determine a non-uniformity of the beam of X-rays, and to correct the scattering profile to account for the non-uniformity.

13. Apparatus for inspection of a sample, comprising:
   an X-ray source, which is arranged to direct a beam of X-rays toward a sample;
   an array of detector elements, which are arranged along an array axis and mutually separated by a predetermined pitch, and which are arranged to capture the X-rays scattered from the sample;
   a motion stage, which is adapted to move the sample in a direction parallel to the array axis between at least first and second positions, which positions are separated one from another by an increment that is not an integer multiple of the pitch;
   a shutter assembly, which is arranged to reduce a transverse dimension of the beam, wherein the shutter assembly is shifted in conjunction with shifting the sample; and
   a processor, which is coupled to receive at least first and second signals generated by the detector elements responsively to the X-rays captured thereby while the sample is in at least the first and second positions, respectively, and which is operative to combine at least the first and second signals so as to determine an X-ray scattering profile of the sample as a function of position along the axis.

14. The apparatus according to claim 13, wherein the shutter assembly comprises a knife edge, which is positioned at a selected distance from a surface of the sample, and which is adapted to move in conjunction with shifting the sample so as to maintain the selected distance between the knife edge and the surface.

* * * * *